United States Patent [19]

Kawai et al.

[11] Patent Number: 5,763,684
[45] Date of Patent: Jun. 9, 1998

US005763684A

[54] METHOD OF PURIFYING FLUOROMETHYL-1,1,1,3,3,3-HEXAFLUOROISOPROPYL ETHER

[75] Inventors: Toshikazu Kawai; Mineo Watanabe; Manami Kobayashi, all of Saitama, Japan

[73] Assignee: Central Glass Co., Ltd., Yamaguchi, Japan

[21] Appl. No.: 913,507

[22] PCT Filed: Jan. 22, 1997

[86] PCT No.: PCT/JP97/00128

§ 371 Date: Sep. 16, 1997

§ 102(e) Date: Sep. 16, 1997

[87] PCT Pub. No.: WO97/27165

PCT Pub. Date: Jul. 31, 1997

[30] Foreign Application Priority Data

Jan. 23, 1996 [JP] Japan .................................. 8-009515

[51] Int. Cl.⁶ .................................................. C07C 41/00

[52] U.S. Cl. ........................................ 568/682; 568/683
[58] Field of Search ............................ 568/682, 683

[56] References Cited

U.S. PATENT DOCUMENTS

4,250,334  2/1981  Coon et al. ............................ 568/683
5,684,210  11/1997 Kawai et al. .......................... 568/682

FOREIGN PATENT DOCUMENTS

7-258138  10/1995  Japan .

*Primary Examiner*—Gary Geist
*Assistant Examiner*—Sreeni Padmanabhan
*Attorney, Agent, or Firm*—Evenson, McKeown, Edwards & Lenahan P.L.L.C.

[57] ABSTRACT

The present invention relates to a method of removing bisfluoromethyl ether contained in fluoromethyl-1,1,1,3,3,3-hexafluoroisopropyl ether in a simple, effective manner, and is characterized in that fluoromethyl-1,1,1,3,3,3-hexafluoroisopropyl ether containing bisfluoromethyl ether is brought into contact with zeolite.

3 Claims, No Drawings

METHOD OF PURIFYING FLUOROMETHYL-1,1,1,3,3,3-HEXAFLUOROISOPROPYL ETHER

This is the U.S. National Stage Application of PCT/JP97/00128 filed Jan. 22, 1997 now WO97/27165 published Jul. 31, 1997.

TECHNOLOGICAL FIELD

The present invention relates to a method of purifying fluoromethyl-1,1,1,3,3,3-hexafluoroisopropyl ether, which is widely used as a pharmaceutical and particularly as an inhalation anesthetic.

BACKGROUND TECHNOLOGY

Hitherto, fluoromethyl-1,1,1,3,3,3-hexafluoroisopropyl ether has widely been used as a safe inhalation anesthetic. In use of such inhalation anesthetic, it is demanded that impurity is essentially not contained therein. In order to achieve this aim, a method of improving the purity of fluoromethyl-1,1,1,3,3,3-hexafluoroisopropyl ether was eagerly continuously examined. As a result, when fluoromethyl-1,1,1,3,3,3-hexafluoroisopropyl ether is produced from 1,1,1,3,3,3-hexafluoroisopropyl alcohol, hydrogen fluoride, formaldehyde, and concentrated sulfuric acid or another dehydrating agent, in accordance with the description of U.S. Pat. No. 4,250,334, it was found that fluorinated ethers, except fluoromethyl-1,1,1,3,3,3-hexafluoroisopropyl ether, and high-boiling-point polyethers are inevitably produced, as well as the by-products, such as formal and acetal, which are described in the above-mentioned patent specification, and that, of these, particularly the fluorinated ethers as by-products suppress the improvement of the purity of fluoromethyl-1,1,1,3,3,3-hexafluoroisopropyl ether. With regard to most of these by-products, it is usual that they receive the chemical or physical action and thus essentially do not remain in the product, by conducting the recovery treatment method, i.e. water washing, alkali washing, drying, distillation and the like, which is usually used against such reaction products. There has been found an unexpected property troublesome in the purification treatment, in which, although among the fluorinated ethers as by-products, bisfluoromethyl ether alone is an extremely unstable compound, when it coexists with fluoromethyl-1,1,1,3,3,3-hexafluoro-isopropyl ether, it is not separated by the above-cited usual recovery treatment method. Thus, when the purification was tried by distilling fluoromethyl-1,1,1,3,3,3-hexafluoroisopropyl ether containing bisfluoromethyl ether, contrary to the expectation, it was confirmed that bisfluoromethyl ether and fluoromethyl1,1,1,3,3,3-hexafluoroisopropyl ether do not easily separate from each other and show an azeotropic behavior.

Thus, the present inventors have already proposed in JP-A-7-258138 a method of purifying fluoromethyl-1,1,1,3,3,3-hexafluoroisopropyl ether by treating a fluoromethyl-1,1,1,3,3,3-hexafluoroisopropyl ether containing at least bisfluoromethyl ether with one or at least two of a Broensted acid, a Lewis acid, or an acid fixed to a resin or the like. This method is effective in decreasing the bisfluoromethyl ether content. It is, however, necessary to treat newly produced by-products, due to the use of a chemical change caused by the reaction. Therefore, the position of the above step may be limited in the production process, or the cost may increase due to the complication of the process.

Therefore, the present invention's task is the provision of a method of removing bisfluoromethyl ether contained in fluoromethyl-1,1,1,3,3,3-hexafluoroisopropyl ether, in an easy, effective manner.

DISCLOSURE OF THE INVENTION

In view of the above-mentioned prior art problems, the present inventors have eagerly examined a purification method for obtaining a fluoromethyl-1,1,1,3,3,3-hexafluoroisopropyl ether essentially not containing bisfluoromethyl ether, without having an adverse effect on fluoromethyl-1,1,1,3,3,3-hexafluoroisopropyl ether. As a result, we have found that, if the fluorinated ether formed as a by-product in the synthesis of fluoromethyl1,1,1,3,3,3-hexafluoroisopropyl ether is contacted with zeolite, it is efficiently removed. Thus, we have achieved the present invention.

In other words, the present invention provides a method of purifying fluoromethyl-1,1,1,3,3,3-hexafluoroisopropyl ether, characterized in that bisfluoromethyl ether contained in fluoromethyl-1,1,1,3,3,3-hexafluoroisopropyl ether is removed by contact with zeolite.

As zeolite used for removing bisfluoromethyl ether in the present invention, there are cited those of faujasite group, chabazite group, mordenite group and the like. As faujasite group, there can be cited natural zeolites, such as faujasite, and synthetic zeolites, such as A-types (e.g., 3A, 4A and 5A), X-types (e.g., 10X and 13X) and Y-types. As chabazite group, there can be cited natural zeolites, such as chabazite, gmelinite, erionite and levynite, and synthetic zeolites, such as R-types, S-types or T-types. As mordenite group, there can be cited natural or synthetic mordenites, clinoptilolite and the like.

Furthermore, it is possible to selectively use various modifications of zeolites of each type, such as commercial acid-resistant grades, heat-resistant grades and the like, which are obtained, for example, by changing the Si/Al ratio or by conducting an after-treatment subsequent to the zeolite synthesis or after the baking.

Of these, synthetic zeolites of faujasite group are preferable, and synthetic zeolites 3A, 4A, 10X, 13X and the like, which are easily obtained, are particularly preferable.

Zeolite used in the invention may take an either form of powder, granule, pellet and the like. In particular, when it is used in a packed column, spherical or elongate ones, which have been subjected to molding and baking together with a granulating agent such as clay or CMC (carboxymethylcellulose), are easy to be handled and preferable.

The manner of contacting fluoromethyl-1,1,1,3,3,3-hexafluoroisopropyl ether and zeolite is not limited, and there are cited, for example, a batch-type method in which they are brought into contact for a predetermined period of time by adding zeolite to fluoromethyl-1,1,1,3,3,3-hexafluoroisopropyl ether in a container, with stirring or without stirring, and a flow-type method in which fluoromethyl-1,1,1,3,3,3-hexafluoroisopropyl ether is allowed to flow through a container packed with zeolite. The treatment temperature is not particularly limited, but is required to be the melting temperature or higher. Thus, it is from 40° to 100° C., preferably from −40° to 60' C. When the treatment is conducted under about normal pressure, it is the most preferable to conduct that at a temperature of from −20° to 40° C., in view of the equipment and the maintenance of quality of fluoromethyl-1,1,1,3,3,3-hexafluoroisopropyl ether. To be higher than 100° C. is not preferable, because fluoromethyl-1,1,1,3,3,3-hexafluoroisopropyl ether may be decomposed. The treatment pressure does not bring a particular effect on the treatment result. Therefore, it may be an arbitrary pressure, and in general it is conducted under a pressure of from 1 to 10 kg/cm$^2$.

In the flow-type method, the linear velocity of liquid is approximately within a range of from 1 cm/hr to 10 m/hr, preferably from 2 cm/hr to 5 m/hr. A linear velocity slower than 1 cm/hr is not preferable because the treatment time becomes long, and that exceeding 10 m/hr is not preferable because the period of time of flow becomes short.

In the batch-type method, the treatment time depends on the content of bisfluoromethyl ether, the amount of zeolite added to fluoromethyl-1,1,1,3,3,3-hexafluoroisopropyl ether, and the treatment temperature. It ranges from 10 minutes to 100 hr, preferably from 20 minutes to 50 hr, more preferably from 30 minutes to 10 hr. The amount of zeolite added thereto is not particularly limited, and the weight ratio of zeolite to fluoromethyl-1,1,1,3,3,3-hexafluoroisopropyl ether is preferably from 0.001 to 0.5. If it is 0.001 or less, it takes a long time for the treatment. To be 0.5 or more does not particularly bring a technological disadvantage, but is economically not preferable.

Fluoromethyl-1,1,1,3,3,3-hexafluoroisopropyl ether, to which the present invention is applied, contains at least bisfluoromethyl ether. The content is generally from 1 ppm to 5 wt %, but is not particularly limited because it varies depending on the production method, the production condition and the like. According to the method of the present invention, it is possible to decrease the content of bisfluoromethyl ether to not higher than 1 ppm. It is preferable to use a fluoromethyl-1,1,1,3,3,3-hexafluoroisopropyl ether, which acid substance has previously been removed from, and which has been synthesized from a mixture of formaldehyde or its polymer and 1,1,1,3,3,3-hexafluoroisopropyl alcohol, in the presence of an acid such as sulfuric acid, or has been synthesized from bisfluoromethyl ether and 1,1,1,3,3,3-hexafluoroisopropyl alcohol. Furthermore, fluoromethyl-1,1,1,3,3,3-hexafluoroisopropyl ether may be one that has been subjected to a purification treatment such as decomposition, adsorption or absorption of the by-products or to a separation purification treatment such as distillation. In the method of the present invention, it is preferable that water contained in fluoromethyl-1,1,1,3,3,3-hexafluoroisopropyl ether is less in amount, but the water content to an extent of saturation is not particularly problematic.

According to the present invention, it is possible to remove bisfluoromethyl ether contained in fluoromethyl-1,1,1,3,3,3-hexafluoroisopropyl ether, using a simple device and an easy operation, in which the liquid to be treated is brought into contact with zeolite in a batch-type or flow-type manner.

THE BEST MODE TO CARRY OUT THE INVENTION

Hereinafter, the present invention will clearly be described with reference to Examples, but the present invention is not limited thereto. The analysis was conducted by gas chromatography. In Examples, all of "%" refer to weight %.

[Exemplary Preparation of fluoromethyl-1,1,1,3,3,3-hexafluoroisopropyl ether]

A 5-liter reaction vessel was charged with 500 ml of 98% sulfuric acid, 1000 g (50 mol) of hydrogen fluoride, and 300 g (10 mol) of paraformaldehyde. This reaction mixture was heated to 65° C. Then, 1680 g (10 mol) of 1,1,1,3,3,3-hexafluoroisopropyl alcohol was added on a dropwise basis, over 2 hr, with stirring. Vapors generated by the reaction were collected by leading them to a trap containing water. With this, 1410 g of crude fluoromethyl-1,1,1,3,3,3-hexafluoroisopropyl ether was obtained. This crude fluoromethyl-1,1,1,3,3,3-hexafluoroisopropyl ether contained 0.62% of bisfluoromethyl ether and 10.6% of polyethers. Furthermore, the water content was 0.13%.

[EXAMPLE 1]

A 100 ml reaction vessel was charged with 50 g of crude fluoromethyl-1,1,1,3,3,3-hexafluoroisopropyl ether obtained in the Exemplary Preparation. Then, 5 g of a synthetic zeolite (molecular sieve 13X of Wako Junyaku Co.) having a particle diameter of about 2 mm was added thereto, followed by standing still for 3 hr. After that, it was analyzed with a gas chromatograph. With this, it was not possible to detect bisfluoromethyl ether, because it was not higher than the detection limit (1 ppm). At this stage, the water content has decreased to 0.002%. Furthermore, new by-products were not found.

[EXAMPLE 2]

600 g of fluoromethyl-1,1,1,3,3,3-hexafluoroisopropyl ether, which was obtained in the Exemplary Preparation, was distilled. With this, there was obtained fluoromethyl-1,1,1,3,3,3-hexafluoroisopropyl ether containing as main distillates 0.58% of bisfluoromethyl ether, 0.01% of polyethers and 0.09% of water.

This crude fluoromethyl-1,1,1,3,3,3-hexafluoroisopropyl ether was allowed to flow at a rate of 60 g/hr through a glass column that has an inner diameter of 2 cm and is packed with 100 g of a synthetic zeolite (ZEOLAM A-4 made by TOSOH CORP.) having a particle diameter of about 2 mm. With this, bisfluoromethyl ether was not higher than the detection limit, and the water content was 0.001%. Furthermore, new by-products were not found.

We claim:

1. A method of purifying fluoromethyl-1,1,1,3,3,3-hexafluoroisopropyl ether, characterized in that fluoromethyl-1,1,1,3,3,3-hexafluoroisopropyl ether containing bisfluoromethyl ether is brought into contact with zeolite.

2. A method of purifying fluoromethyl-1,1,1,3,3,3-hexafluoroisopropyl ether according to claim 1, wherein said zeolite is a zeolite of faujasite group.

3. A method of purifying fluoromethyl-1,1,1,3,3,3-hexafluoroisopropyl ether according to claim 1, wherein said zeolite is a synthetic zeolite 3A, 4A, 10X or 13X.

* * * * *